United States Patent [19]
Barrett et al.

[11] Patent Number: 5,336,261
[45] Date of Patent: Aug. 9, 1994

[54] CORNEAL INLAY LENSES

[75] Inventors: Graham D. Barrett, Perth, Australia; William J. Link, Irvine; Cary J. Reich, Laguna Hills, both of Calif.

[73] Assignee: Chiron IntraOptics, Inc., Irvine, Calif.

[21] Appl. No.: 15,984

[22] Filed: Feb. 10, 1993

Related U.S. Application Data

[63] Continuation-in-part of Ser. No. 759,599, Sep. 16, 1991, Pat. No. 5,196,026.

[51] Int. Cl.$^5$ .............................................. A61F 2/14
[52] U.S. Cl. ........................................................ 623/5
[58] Field of Search .................................... 623/4, 5

[56] References Cited

U.S. PATENT DOCUMENTS

| | | | |
|---|---|---|---|
| 4,607,617 | 8/1986 | Choyce | 128/1 R |
| 4,624,669 | 11/1986 | Grendahl | 623/5 |
| 4,676,790 | 6/1987 | Kern | 623/5 |
| 4,781,187 | 11/1988 | Herrick | 128/305 |
| 4,932,970 | 6/1990 | Portney | 623/6 |
| 4,976,732 | 12/1990 | Vorosmarthy | 623/6 |
| 5,166,711 | 11/1992 | Portney | 351/161 |
| 5,166,712 | 11/1992 | Portney | 351/161 |

*Primary Examiner*—Randy C. Shay
*Attorney, Agent, or Firm*—Rothwell, Figg, Ernst & Kurz

[57] ABSTRACT

A low or high refractive index corneal inlay optical lens adapted to be inserted singly or multiply between the layers of a cornea to correct refractive errors in eyesight, wherein the implanted lens is a solid transparent uncoated lens having no apertures therethrough, of a diameter less than that of the optic zone of the eye under normal light or bright light conditions, such that the movement of fluids, nutrients and gases throughout the corneal layers is unimpeded, and wherein the composition of the lens or lenses relative to that of the surrounding stromal tissue are such that multiple refractive indices may be created and multiple focal corrections are possible.

12 Claims, 3 Drawing Sheets

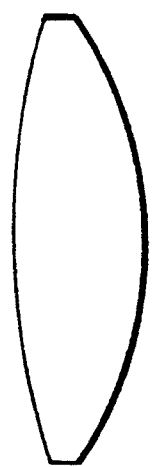
FIG. 3C (+)
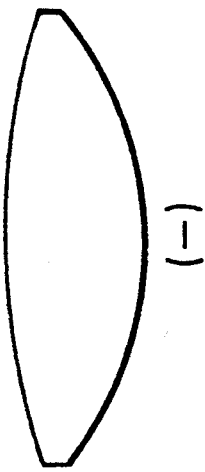
FIG. 3F (−)
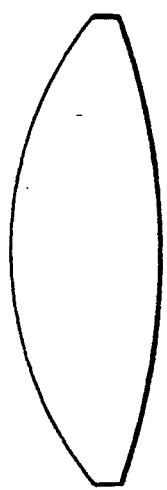
FIG. 3B (+)
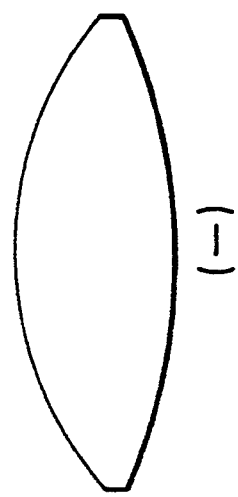
FIG. 3E (−)
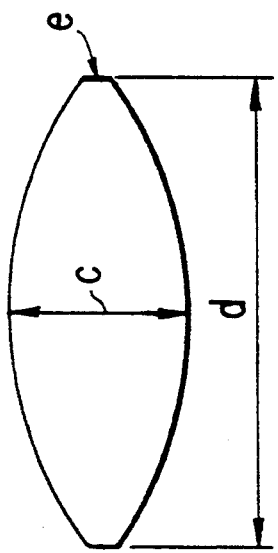
FIG. 3A (+)
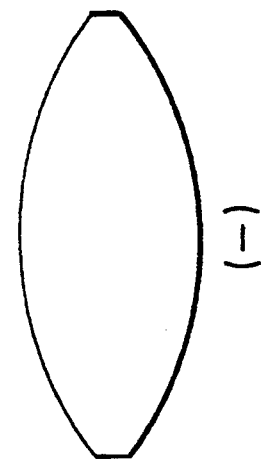
FIG. 3D (−)

CORNEAL INLAY LENSES

This is a continuation-in-part of copending U.S. Patent application Ser. No. 759,599, filed Sept. 16, 1991, now U.S. Pat. No. 5,196,026.

BACKGROUND OF THE INVENTION

1. Field of the Invention

This invention relates to implants designed to be surgically inserted between the layers of the cornea to correct refractive errors. More particularly, the invention relates to corneal implants that can serve as a substitute for conventional spectacles or contact lenses.

2. Description of the Related Art

There have already been proposed artificial lenses for implantation in the eye. Such implants have hitherto been intended, not as corrective lenses, but as a substitute for the natural lens of the eye. For example, when an eye develops a cataract, the natural lens becomes fogged or opaque, thereby impairing vision. When such a cataract is treated, the lens is removed, leaving the eye aphakic. Although it is possible to correct for aphakia using spectacles, the degree of correction requires spectacles so thick as to make them both cumbersome and unattractive. For these reasons, lenses have been designed for correction of aphakia wherein the substitute lens is inserted into the eye during the operation to remove the cataract or at a second operation. Such substitute lenses are of fixed focal length and, as the natural lens has been removed, the eye is no longer capable of accommodation, that is to say, the focal length cannot change to focus at different distances. It is accepted in this field that such implanted lenses are not prescribed as an alternative to conventional spectacles for a person suffering only from myopia or presbyopia.

Another implant that has been used in the past with some success has been the artificial cornea described in U.S. Pat. No. 2,714,712, and generally resembling what is known as a kerato-prosthesis. These implants are designed as a replacement for the natural cornea itself where the cornea has become fogged or opaque, and are not intended to be a substitute for conventional spectacles or contact lenses.

It is known to resort to surgery in order to correct for defects in eyesight. The various procedures for refractive corneal surgery to correct vision problems such as myopia have not gained general acceptance in ophthalmology. These include radial keratotomy introduced in modern times (1972) by Fyodorov of the USSR, keratomileusis introduced in 1961 by Barraguer of Columbia, keratophakia which uses shaped donor corneas as lens, epikeratophakia which uses an epigraft of homologous tissues, keratotomy to correct astigmatism, and removing clear lens. Such surgery does not have a fully predictable outcome, and furthermore any non-spherical flattening of the cornea on healing results in an eyesight defect that cannot be corrected by the use of spectacles or contact lenses.

The human cornea is a transparent avascular tissue about 10-12 mm in diameter. The cornea functions as a protective membrane and as a "window" through which light rays pass en route to the retina. The average adult cornea is about 0.65 mm thick at the periphery and about 0.54 mm thick in the center (optic zone). From anterior (front) to the posterior (back), it has 5 distinct layers: the epithelium which is 5 or 6 cell layers thick; a clear acellular Bowman's layer; the stroma (which constitutes about 90% of the thickness of the cornea); the thin Descemet's membrane; and, the single layer endothelium. Sources of nutrition for the cornea are the blood vessels of the limbus, the aqueous humor and tears. The superficial cornea also gets most of its oxygen from the atmosphere.

The zone in the cornea through which incident light passes is known variously as the "optic zone" or "pupillary aperture," and both terms will be used interchangeably herein. The size of the normal pupil varies at different ages and from person to person, but normally is about 3–4 mm—smaller in infancy, tending to be larger in childhood, and again progressively smaller with advancing age. Vaughan, D., et al., *General Ophthalmology*, 2d ed., Appleton & Lange, Norwalk, CT, 1989, Ch. 15; Choyce, *Cataract*, 7 (June 1985). The size of the pupillary aperture, of course, varies inversely with the amount of incident light.

Disks of many different materials have been inserted into corneal stromal pockets, initially to control corneal edema, but more recently to correct refractive errors. Hydrogel and polysulfone lenses have been more successful than other types of lenses so far tried.

Previous corneal implants for the correction of refractive errors have enjoyed only limited success, in part because of the large diameter of the lenses used and in part because of the composition of such lenses. As will be detailed in the review of the related art below, the ophthalmologically more desirable high refractive index polymeric lenses previously used tend to prevent access of fluids, nutrients and gases such as oxygen to the tissue anterior to the implant and to the corneal tissue posterior to the implant. On the other hand, high water content, low refractive index lenses such as hydrogel lenses, while reducing or eliminating the problem of nutrient and gas transport, are generally not able to provide the necessary corrections in refractive error of the eye. Previous corneal implants have also not been able to provide multifocal refractive correction.

The large diameter of previous corneal implant lenses has also required a less-than-satisfactory surgical approach to implantation. In general, previous corneal inlays have required cutting a large pocket into the cornea and inserting in this pocket the lens which resides predominantly behind Bowman's membrane. With this type of insertion, the large implanted lens distorts the cornea, thereby producing a change in optical power. The disadvantage of such a procedure has been that the distortion is usually in the posterior side of the cornea. Such posterior distortion, however, produces only a very small change in optical power because the difference between the refractive index produced is only the small difference between the inlay/cornea and the aqueous humor.

Choyce, D.P., U.S. Pat. No. 4,607,617, issued Aug. 26, 1986, relates to an implant designed to be inserted between the layers of a cornea of an eye to correct eyesight defects, comprising a polysulfone plastic material of a high refractive index (typically 1.633), of a thickness in the range of 0.1 to 0.4 mm, and capable of being sterilized by steam autoclaving prior to insertion. As the implant is entirely embedded in the cornea, it is said not to be exposed to the atmosphere or to the aqueous humor. The polysulfone material is said to be "relatively permeable to body fluids", although it is not clear that this is so. The lens is inserted by a procedure comprising forming an incision in the outer layer of the cornea, separating layers of the cornea to form a pocket, inserting into this pocket a lens inlay, and resealing the incision. Although Choyce neither discloses nor suggests a specific diameter for the lens inlay, reference to FIG. 7b of the specification shows that this diameter is substantially greater than the optic zone of the cornea, which, as noted above, normally is about 3 mm to 4 mm in diameter. This fact, plus the fact that it is known that high refractive index plastic inlay lenses are poorly permeable to fluids, nutrient materials and necessary gases such as oxygen, limits the usefulness of this inlay lens. Further, this corneal inlay does not provide multifocality.

Grendahl, D.T., U.S. Pat. No. 4,624,699, issued Nov. 25, 1986, relates to a corneal inlay for implantation made of a plastic material such as polysulfone or PMMA. Recognizing that prior art polysulfone inlay lenses are poorly permeable to nutrients, fluids and gases, a property of concern to medicine, the inventor attempts to overcome these disadvantages by providing a corneal inlay with a plurality of holes or slots for passage of nutrients through the cornea. The inlay lens is said to have a diameter of approximately 3 mm to 7 mm, preferably 4.5 mm to 6.5 mm, more preferably slightly less than 6 mm in diameter (column 2, lines 21–26). Inlay lenses of such diameter will generally completely cover the optic zone of a normal human cornea, creating the problems of nutrient and gas supply described above. There is no disclosure or suggestion in this patent that the inlay lens could be smaller than the opening of the optic zone, nor is there reference to any property of the lens other than a single focal distance.

Lindstrom, R.L., U.S. Pat. No. 4,851,003, issued Jul. 25, 1989, discloses corneal inlay lenses applied under the cornea and about the stroma. The lens is fenestrated, and includes a plurality of fixation holes around the periphery and a coating on the anterior surface by a material that enhances the growth of corneal epithelial cells into and about the holes. The coating is composed of biological materials such as fibronectin, laminin, a glycosaminoglycan, or a type IV collagen. Although the diameter of the inlay lenses is not specifically disclosed, the dimensions of the holes (up to 1 mm), taken together with FIG. 6 which shows the epicorneal lens implanted below the epithelium, indicates that the diameter of the inlay lens is at least 5–7 mm, and thus substantially greater than the optic zone of the cornea. Such lenses also do not provide a patient with multiple focalities.

Thus, the prior art inlay lenses are less than satisfactory in important ways. Where large (e.g., 5 mm to 7 mm) hydrogel lenses are used, wherein the water content is high (about 72%) and the index of refraction low (about 1.38), problems of permeability to nutrients and gases are generally less severe, but the dioptic power is low. Where large polymeric lenses are used, wherein the water content is quite low and the refractive index high (e.g., 1.45 to 1.633), the optic power is satisfactory, but the permeability is poor. Such non-permeability to essential nutrients and gases tends to cause "starvation" in the anterior segments of the stroma, ultimately resulting in extrusion of the inserted lens. Although the permeability problem is reduced by placing holes or slots in polymeric lenses (see Grendahl above), such holes interfere with vision. Further, none of the prior art inlay lenses provide for multiple focality, which is highly desirable in many patients.

There remains, therefore, an important need for intra-corneal lenses of a refractive index sufficiently high so as to avoid the need to distort the cornea in order to obtain the desired optical power, of a size sufficiently small so as to simplify surgical insertion, of a diameter that permits essential nutrients and gases readily to reach the anterior of the cornea, and of a type that permits either unifocality or multiple focalities.

Such an intra-corneal inlay lens has been invented, and it and its uses are disclosed below.

SUMMARY OF THE INVENTION

The invention provides a biocompatible, solid, transparent, low or high refractive index corneal inlay lens adapted to be inserted singly or multiply between the layers of the cornea to correct refractive errors, wherein the lens is of a diameter less than that of the optic zone under normal ambient light conditions or preferably under bright light conditions. The size of the lens permits the passage of nutrients and gases from the posterior aspect of the cornea through to the anterior aspect. The lens is of a composition relative to that of the surrounding tissues such that multiple refractive indices may be created and multiple focal corrections are possible.

In accordance with a first aspect of the invention, there is disclosed a corneal lens of a diameter less than that of the corneal optic zone under normal light or bright light conditions, the diameter and compositions of such lens being such that areas of different refractive indices are created in the optic zone, thereby providing multiple focality.

In accordance with yet another aspect the invention, the inventive lenses are used to provide vision corrections in patients.

These and other aspects and objects of the invention will become apparent by reference to the specification below and the appended claims.

DESCRIPTION OF THE DRAWINGS

FIGS. 3A through 3F show biconvex lenses of the invention. Designations "e", "d" and "c" are as in FIG. 2.

DETAILED DESCRIPTION OF THE INVENTION

Figure 1B:
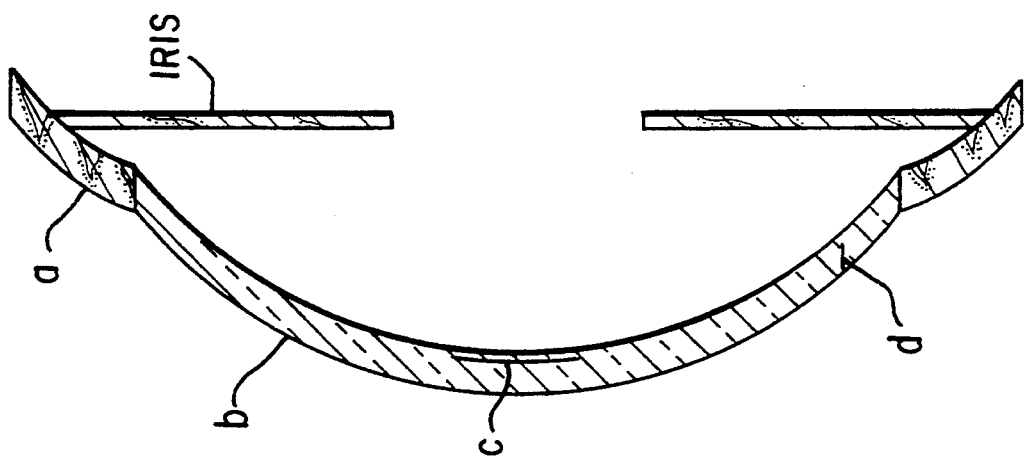
FIGS. 1A and 1B are representations of the anatomic relationship of the inlay lenses of the invention to the cornea. In the figure, "a" is the sclera, "b" the cornea, "c" the inlay lens, and "d" the incision for inlaying the corneal lens.
Figure 1A:
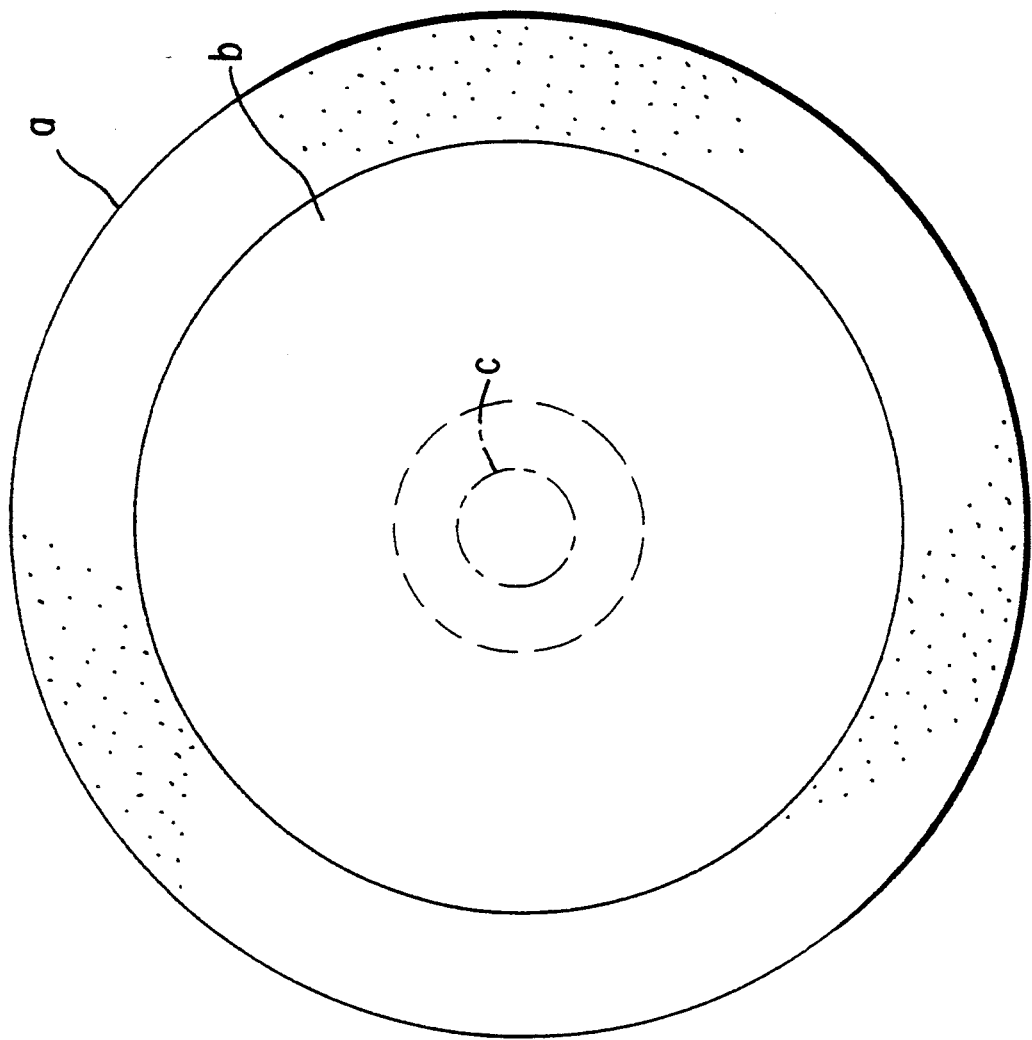

The invention provides bicompatible, solid, low or high refractive index corneal implant corrective lenses of novel dimension, adapted to be surgically inserted into stromal pockets via a very small incision in the corneas of patients suffering from refractive error. Advantageously, the lenses of the invention provide multiple refractive indices and multiple focalities.

A surgical implantation procedure involves making a stromal cut parallel to the limbus of about 2 mm to about 3 mm in length to about 50% to about 95% thickness, preferably about 75% thickness, using a blunt spatula to make a pocket in the stroma to the center of the corneal optic zone (pupillary aperture), inserting the corrective lens into the pocket, then permitting the incision to reseal peripherally to the lens.

The lenses are of a diameter smaller than that of the optic zone of the cornea under normal ambient light or, preferably, under bright light conditions, and are of a size such that the implanted lens or lenses, regardless of composition, water content or index of refraction, will not substantially impede the movement of fluids, nutrients and gases to all layers of the cornea. Typically, the lenses are of a diameter of from about 1 mm to about 3 mm.

The transparent inlay lenses of the invention are solid with no holes or slits, and may be uncoated or coated. Such lenses create regions of different refractive indices within the optic zone, one created by the lens itself and the other by the neighboring stroma tissue, thereby providing a useful multifocal capability. The brain is capable of sorting out the different signals and using the information appropriately. This embodiment is not limited to a single small diameter lens; a mosaic of two or more such lenses may be implanted in the same plane, thereby providing for additional multiple focality.

Multiple focality may be achieved under all lighting conditions where both distance and near vision would be expected to be useful. This would correspond to a minimal pupil size of about 2.0 mm.

The area of the cornea related to near vision should be no more than about 75-80% of the entire functional pupil size in order to retain multiple focal vision under bright light conditions ("blc"). For example, if the patient's pupil diameter under blc is 2.0 mm, then an inlay lens that creates additional power (i.e., the inlay creates an area in the cornea devoted to near vision) should have a diameter of about 1.75 mm. The area devoted to near vision under blc is about 2 4 mm$^2$, while the total area of the optic zone is about 3.14 mm$^2$. Therefore, about 77% of the optic zone of this pupil is devoted to near vision.

Similarly, if the patient's pupil diameter is 2.5 mm under blc, then an inlay with a diameter of 2.16 mm could be used. The pupil size under blc is seldom less than about 2 mm and seldom greater than 3 mm, so for the general population, inlays with a diameter of from about 1.75 mm to about 2.6 mm would be adequate. However, in those rare cases in which, due to trauma, surgery or disease, the pupil size under blc is substantially greater than 3.0 mm, then the size of the desired inlay can be computed and adjusted accordingly so that no more than about 75-80% of the entire functional pupil size is devoted to near vision created by the implantation of the inlay lens or lenses.

Presbyopes will benefit from the multiple focality of the cornea which is produced by the cornea's central zone being altered by the small lens of the invention for near vision, while the unaltered peripheral zone remains responsible for distance vision. Myopic patients can benefit in the reverse way by implanting a negative lens in the center, rendering the small central zone optically less powerful. Hyperopia and aphakia may also be treated with these lenses.

An enormous number of refractive corrections are possible with the lenses of this invention. Positive and negative lenses of all useful diopters may be employed. The lenses may be of a refractive index greater or less than that of the neighboring corneal tissue. Thus this invention can be used to correct presbyopia, myopia, hyperopia, aphakicia, and perhaps other corrections as well.

Figure 2A:
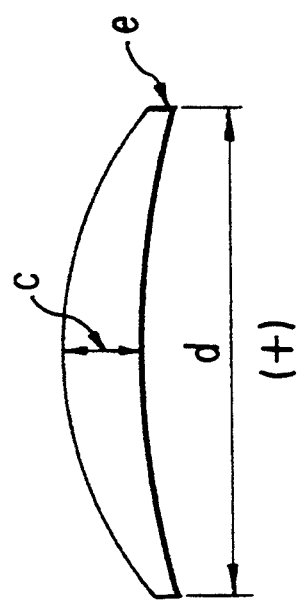
FIGS. 2A through 2D show meniscus lenses of the invention. In the figures, "e" is edge thickness, "d" the diameter, and "c" the center thickness.
Figure 2C:
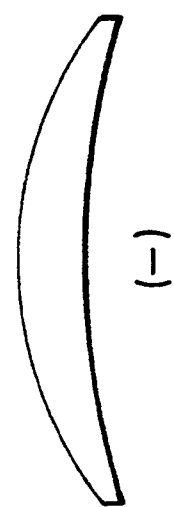
Figure 2B:
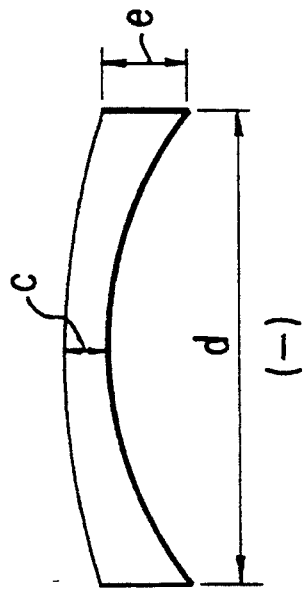
Figure 2D:

Meniscus and biconvex lenses are preferred. FIG. 2 shows the designs of meniscus lenses of the invention. FIG. 2A shows meniscus designs when the R.I. of the lens is greater than that of the surrounding corneal tissue, while FIG. 2B shows meniscus designs when the R.I. of the lens is less than that of adjacent corneal tissue. In both figures, "d", the lens diameter, ranges between about 1 mm and about 3 mm, preferably between about 1.75 mm and about 2.6 mm, "e" the edge thickness, ranges between about 0 005 mm and about 0.05 mm; and, "c", the center thickness ranges between about 0.01 mm and about 0.25 mm. The refractive power, P, varies depending on the type of lens design (meniscus or biconvex) and the type of lens material. From d, e, c, and P, anterior and posterior radii of the lens can be calculated by standard methods.

FIG. 3 shows the design of the biconvex lenses of the invention. FIG. 3A shows biconvex design where the R.I. of the lens is greater than that of the adjacent corneal tissue, while FIG. 3B shows biconvex designs when the R.I. of the lens is less than that of the surrounding corneal tissue. Dimensions "d", "e" and "c" are defined in FIG. 2.

Referring to FIG. 2A, in the left hand sketch there is shown a positive "(+)" lens in which P= +0.5 to +20.00. In the right hand sketch of FIG. 2A, there is shown a negative "(−)" lens in which P= −0.5 to −20.0 diopters. In the left hand sketch of FIG. 2B, there is shown a (−) lens in which P= −20.0 to −0.5 diopters, whereas the anterior radius and posterior radius can both range from flat (infinite) to about 5 mm. In the right hand sketch of FIG. 2B, there is shown a (+) lens in which P= +20.0 to +0.5 diopters.

Referring to FIG. 3, in the left hand sketch of FIG. 3A, the radii of the anterior and posterior surfaces are equal, whereas in the middle sketch the anterior radius is greater than that of the posterior radius, and in the right hand sketch the anterior radius is less than that of the posterior radius; all lenses are (+), and P= +0.05 to +20.0 diopters. The three sketches in FIG. 3B are the counterparts of those in FIG. 3A, but because of the opposite relationships of the R.I.s, all lenses are (−), and P= −20.0 to −0.05 diopters.

Biconcave lenses may also be used. The relationships between the R.I. of the lenses and that of the adjacent corneal tissue are as described in FIGS. 2 and 3. Likewise, the availability of (+) or (−) corrective lenses and powers are also as described in FIGS. 2 and 3.

As noted above, because of their small diameter or configuration, the lenses made in accordance with this invention avoid the problems of fluid, nutrient and gas passage attendant upon prior art corneal implant lenses, no barriers to transport being present. Thus, the invention provides a great deal of flexibility in the selection of lens composition, refractive index and water content.

Lenses may be composed of gels such as hydrogels, polymeric materials, cellulose esters and silicones. One may use hydrogels of low water content or high water content. In one embodiment, one may use a hydrogel lens of low water content, a diameter of about 2 mm, a center thickness of about 0.02-0.05 mm, a R.I. of 1.42 to 1.43, and a power of +2.5 D in the stroma to correct for presbyopia. High water content materials of R.I. slightly greater than or less than the R.I. of the stroma may also be used by an appropriate choice of design. Also suitable are non-water containing polymeric material such as the high R.I., relatively rigid polysulfones (e g , UDEL ™, Union Carbide Corp., R.I. typically 1.633) whose high R.I. allows corrections of up to +10 D with a lens 0.04 mm thick, and a correction of −10 D with a differently shaped lens with a thickness of only 0.01 mm at its center. Other suitable polymeric materials include polyethersulfones (VICTREX TM, ICI), polyarylsulfones, PERSPEX CQ TM or PERSPEX CQUV TM (ICI) (R.I. 1.49), polycarbonates, silicones, fluoropolymers, polymethyl methacrylates (PMMA), cellulose acetate or butyrate, or other like materials.

The following examples are merely exemplary of the invention and are in no way intended to limit the scope of the invention which is defined by the specification and the appended claims.

EXAMPLE 1

INSERTION OF A PMMA LENTICULE IN THE CORNEA OF RABBITS' EYES

Physical Parameters:
Design: Meniscus
Material: PMMA
Diameter: 2.0 mm; edge thickness: 0.02 mm; center thickness: 0.022 mm; Base curve: 7.6 mm; P: +2.5D.
Sterilization:
gamma radiation 2.5–3 Mrad due to the thinness of the lenticule; the slight yellowng of the PMMA is negligible.
Implant Procedure:
1.1 Surgical Procedure
Made a 2 mm incision approximately 75% of the stromal thickness about 1 mm central from the limbus in clear cornea. Using a blunt spatula, made a pocket to the center of the cornea.
1.2 Intraoperatve Drug Treatment
The resulting wound was then rinsed with irrigating solution.
1.3 Lens Placement
Prior to placing the lens, several drops of irrigating solution were placed on the eye. The appropriate lens was poured into a wire strainer and rinsed with sterile saline. Several drops of irrigating solution were placed on the lens. The lens was carefully picked up wth a non-toothed forceps and inserted in the pocket. The lens was then moved to the center of the cornea. Care was taken to ensure that the lens is well centered.
1.4 Completion
Flushed the eye well with irrigating solution. Sutured if necessary. Applied two (2) drops of postoperative drug solution.
1.5 Postoperative Treatment
Gave Maxidex 2X daily (weekend treatment is once daily), and antibiotics as necessary.

EXAMPLE 2

INSERTION OF HYDROGEL LENTICULE IN THE CORNEA OF RABBITS' EYES

Physical Parameters:
Design: Meniscus
Material: Hefilcon A (hydrogel with water content: 45%; Refractive Index: 1.425)
Diameter: 2.0 mm; edge thickness: 0.02 mm; center thickness: 0.023 mm; Base curve: 7.6 mm; P: +2.5D.
Sterilization method:
Autoclaving The implant procedures and post-operative treatment were as in Example 1.

EXAMPLE 3

INSERTION OF A HYDROGEL LENTICLE IN THE CORNEA OF CATS' EYES

Physical Parameters:
Design: Biconvex
Material: Hefilcon A (hydrogel with water content: 45%; Refractive Index: 1.425)
Diameter: 2.0 mm; edge thickness: 0.02 mm; center thickness: 0.04 mm; Anterior radius: 7.0 mm; Posterior radius: 9.8 mm; P: +2.5D.
Sterilization method:
Autoclaving
Implant Procedure:
3.1 Surgical Procedure
Made a 2 mm incision approximately 90% of the stromal thickness about 1 mm central from the limbus in clear cornea. Using a blunt spatula, made a pocket to the center of the cornea.
3.2 Intraoperative Drug Treatment
The resulting wound was then rinsed with irrigating solution.
3.3 Lens Placemnt
Prior to placing the lens, several drops of irrigating solution were placed on the eye. The appropriate lens was poured into a wire strainer and rinsed with sterile saline. Several drops of irrigating solution were placed on the lens. The lens was carefully picked up with a non-toothed forceps and inserted in the pocket. The lens was then moved to the center of the cornea. Care was taken to ensure that the lens is well centered.
3.4 Completion
Flushed the eye well with irrigating solution. Sutured if necessary. Applied two (2) drops of postoperative drug solution.
3.5 Postoperative Treatment
Gave Maxidex 2X daily (weekend treatment is once daily), and antibiotics as necessary.

We claim:

1. A corneal implant lens for surgical implantation between the layers and in the optic zone of a cornea of an eye to correct refractive errors in a patient, comprising a solid transparent optical lens having no apertures therethrough, of a diameter such that the entire optic zone of said cornea is not covered by said lens, wherein the diameter of said lens is substantially less than the diameter of said optic zone of said cornea, and wherein when implanted in the eye multiple refractive indices and multiple focalities are created only by the presence or absence of said lens.

2. A lens of claim 1 wherein said diameter of said lens is less than the diameter of said optic zone under bright light conditions.

3. A lens of claim 1, wherein said lens is selected from the group consisting of meniscus, biconvex and biconcave lenses.

4. A lens of claim 1, wherein said diameter of said lens is between about 1 mm and about 3 mm, the edge thickness is between about 0.005 mm and about 0.05 mm, and the center thickness is between about 0.01 mm and about 0.25 mm.

5. A lens of claim 1, wherein said diameter of said lens is between about 1 mm and about 2 mm.

6. A lens of claim 4, wherein said diameter of said lens is between about 1.7 mm and about 2.6 mm.

7. A lens of claim 1, wherein the diopter of said lens is of a positive or negative power.

8. A lens of claim 7, wherein said positive or negative diopter power ranges from about 0.5 to about 20.0.

9. A lens of claim 1, wherein said refractive index of said lens is less or greater than that of the adjacent corneal tissue.

10. A lens of claim 1, wherein said lens is selected from the group consisting of a biocompatible gel, polymeric material, cellulose ester and silicone.

11. A lens of claim 10, wherein said lens is a gel and said gel is a hydrogel.

12. A lens of claim 10, wherein said lens is a polymeric material and said polymeric material is selected from the group consisting of polysulfone, polyethersulfone, polyarylsulfone, polycarbonate, fluoropolymer and polymethyl methacrylate.

* * * * *

UNITED STATES PATENT AND TRADEMARK OFFICE
CERTIFICATE OF CORRECTION

PATENT NO. : 5,336,261
DATED : August 9, 1994
INVENTOR(S) : Graham D. Barrett et al.

It is certified that error appears in the above-identified patent and that said Letters Patent is hereby corrected as shown below:

Col. 5, line 33, change "2 4" to -- 2.4 --.

Col. 6, line 8, change "0 005" to -- 0.005 --.

Col. 7, line 25, change "yellowng" to -- yellowing --.

Signed and Sealed this

Twenty-eight Day of March, 1995

Attest:

BRUCE LEHMAN

*Attesting Officer*     *Commissioner of Patents and Trademarks*